US005723326A

United States Patent [19]

Moon et al.

[11] Patent Number: 5,723,326

[45] Date of Patent: Mar. 3, 1998

[54] GENOME CODING PHYTOLACCA ANTIVIRAL PROTEIN AND A RECOMBINANT EXPRESSION VECTOR THEREFOR

[75] Inventors: Young-Ho Moon, Kyunggi-Do; Hong-Seob Jeon, Seoul; Kyu-Whan Choi, Seoul; Kwan-Ho Lee, Seoul; Man-Keun Kim, Seoul, all of Rep. of Korea

[73] Assignee: Jinro Limited, Seoul, Rep. of Korea

[21] Appl. No.: 471,564

[22] Filed: Jun. 6, 1995

Related U.S. Application Data

[60] Continuation of Ser. No. 210,396, Mar. 17, 1994, abandoned, which is a division of Ser. No. 138,636, Oct. 15, 1993, Pat. No. 5,348,865.

[30] Foreign Application Priority Data

Aug. 28, 1993 [KR] Rep. of Korea ........................ 93-16938

[51] Int. Cl.$^6$ ............................ C12N 9/22; C07K 14/415

[52] U.S. Cl. .......................... 435/199; 530/370; 530/379; 435/69.1; 435/320.1; 435/69.2; 536/23.2; 536/23.6

[58] Field of Search .................................... 435/199, 69.1, 435/320.1, 69.2; 530/370, 379; 536/23.2, 23.6

[56] References Cited

PUBLICATIONS

J.D. Irvin — Purification and Partial Characterization of the Antiviral Protein from Phytolacca americana which inhibits Eukaryotic Protein Synthesis; Arch. Biochem. Biophys., 169, 522–528 (1975).

K.C. Halling et al. — Genomic Cloning and Characterization of a Ricin Gene from Ricinus communis; Nucleic Acid Res., 13, 8019–8033 (1985).

J. Katoaka et al. — DNA Sequence of Mirabilis Antiviral Protein (MAP), a Ribosome-inactivating Protein with an Antiviral Property, from Mirabilis jalapa L. and Its Expression in Escherichia coli; J. Biol. Chem., 266, 8426–8430 (1991).

X. Zhang et al. — Homology of Trichosanthin and Ricin A Chain; Nature, 321, 477–478 (1986).

Y.Endo et al. — The RNA N-Glycosidase Activity of Ricin A–Chain; J. Biol. Chem., 263, 8735–8739 (1988).

J.D. Irvin et al. — Purification and Properties of a Second Antiviral Protein from Phytolacca americana Which inactivates Eukaryotic Ribosomes: Arch. Biochem. Biophys., 200, 418–425 (1980).

B. Jansen et al. — Establishment of a Human t(4;11) Leukemia in Severe Combined Immunodeficient Mice and successful Treatment Using Anti–CD19 (B43)–Pokeweed Antiviral Protein Immunotoxin; Cancer Res., 52, 406–412 (1992).

Y.W. Kim et al. — Immunoconjugates That Neutralize HIV Virions Kill T cells infected with Diverse Strains of HIV–1: J.Immunol., 144, 1257–1262 (1990).

D.E. Myers et al. — Production of a Pokeweed Antiviral Protein(PAP)–containing Immunotoxin, B43–PAP, Directed Against the CD19 Human B Lineage Lymphoid Differentiation Antigen in Highly Purified Form for Human Clinical Trails; J. Immunol. Methods, 136, 221–238 (1991).

M.P. Ready et al. — Extracellular Location of Pokeweed Antiviral Protein; Proc. Natl. Acad. Sci. USA, 83, 5053–5056 (1986).

Q. Lin et al. — Isolation and characterization of a cDNA Clone Encoding the Anti-viral Protein from Phytolacca americana; Plant Mol. Biol., 17, 609–614 (1991).

*Primary Examiner*—Robert A. Wax
*Assistant Examiner*—Rebecca Prouty
*Attorney, Agent, or Firm*—Darby & Darby

[57] ABSTRACT

The present inventors discovered a novel genome coding *Phytolacca insularis* antiviral protein(PIP) isolated from *Phytolacca insularis* Nakai; and developed a recombinant vector for said PIP genome expression and a microorganism transformed therewith. PIP genome of the present invention has nucleotide homology of about 82%, compared with the genome of *Phytolacca americana* antiviral protein isolated from *Phytolacca americana* L., which is closely related to the *Phytolacca insularis* Nakai. PIP cDNA is consist of 918 bp of one open reading frame and termination codon; and polyadenylation signal which is ubiquitous in mRNA of most plants and animals, appears to be located in the upstream of 33 bp from the polyadenylation site. Recombinant PIP of the invention was proved to inhibit the growth of *E. coli* HB101 transformed with said expression vector.

2 Claims, 6 Drawing Sheets

FIG. 2A

```
ATGAAGTTGATGCTTGTGGTGACAATATCAGTATGGCTCATTCTTGCACCAACATCTACT
 M  K  L  M  L  V  V  T  I  S  V  W  L  I  L  A  P  T  S  T

TGGGCCGTGAATACCATCATCTACCATGTTGGAAGTACCACCATTAGAAACTATGCAACT
 W  A  V  N  T  I  I  Y  H  V  G  S  T  T  I  R  N  Y  A  T

TTTGGATACTTCGTACTGAAGGCGAAGATCCAAGTTATGTGCTATGGAATACCAATGCTG
 F  G  Y  F  V  L  K  A  K  I  Q  V  M  C  Y  G  I  P  M  L

CCCAATATTGGATCAAATCCAAAATACATATTGGTTGAGCTCCAAGGTTCAAATGAAGAA
 P  N  I  G  S  N  P  K  Y  I  L  V  E  L  Q  G  S  N  E  E

GGCATCACACTAATGCTAAGACGAAACAATTTATATGTGATGGGCTATTCTGATCCCTAC
 G  I  T  L  M  L  R  R  N  N  L  Y  V  M  G  Y  S  D  P  Y

AACAATAGGTGTCGTTTCCATCTCTTTAAGGCTATCTCAGGTACTGAACGCGAAGATGTA
 N  N  R  C  R  F  H  L  F  K  A  I  S  G  T  E  R  E  D  V

GAGACTACTCTTTGCCCAAATGCCGATTCTCGTGTTGGTAAAAACATAAACTATGATAGT
 E  T  T  L  C  P  N  A  D  S  R  V  G  K  N  I  N  Y  D  S

CGATATCCAACATTGGAATCAAAAGCAGGAGTAAATTCAAGAAGTCGAGTCCAACTGGGA
 R  Y  P  T  L  E  S  K  A  G  V  N  S  R  S  R  V  Q  L  G
```

ATTCGAATACTCGACAGTGGCATTGGAAGGATTTCTGGAGTGACGTCATTCACTGAGAGA
I R I L D S G I G R I S G V T S F T E R

ACCGAAGCTGAATTCCTACTGGTAGCCATACAAATGGTATCAGAGGCAGCAAGATTCAAG
T E A E F L L V A I Q M V S E A A R F K

TACATAGAGGATCAAGTGAAAACTAATTTTAACAGACCATTCAACCCTAATCCCAAAGTA
Y I E D Q V K T N F N R P F N P N P K V

CTTATATTGCAGGAGACATGGGGTAAGATTTCTTCAGCAATTCATGGTGCCAGGAATGGA
L I L Q E T W G K I S S A I H G A R N G

GTTTTACCCAATCCTCTACAGCTAGTGCATGCCAATGGTGCAAATTGGATAGTGTTGAGA
V L P N P L Q L V H A N G A N W I V L R

GTGGATGAAATCAAGCCTGATGTGTCACTCTTAAACTACGTTATTGGGAGCTGCCAGAGA
V D E I K P D V S L L N Y V I G S C Q R

ACTTATAACCAAAATGCCATGTTTTCTCAACTTATAATGTCTACTTATTATAATTACATG
T Y N Q N A M F S Q L I M S T Y Y N Y M

GCTAATCTTGGTGATTAG
A N L G D *

FIG. 3

| Ribosome Inactiving Proteins(RIPs) | Amino Acid Sequence | | | | | | | | | | | | | |
|---|---|---|---|---|---|---|---|---|---|---|---|---|---|---|
| PIP | A | I | Q | M | V | S | E | A | A | R | F | K | Y | I |
| cPAP | A | I | Q | M | V | S | E | A | A | R | F | K | Y | I |
| α-PAP | A | I | Q | M | V | S | E | A | A | R | F | K | Y | I |
| PAP-S | A | I | Q | M | V | S | E | A | A | R | F | K | Y | I |
| MAP | A | I | Q | M | V | S | E | A | A | R | F | K | Y | I |
| Abrin A | I | I | Q | M | V | A | E | A | A | R | F | R | Y | I |
| Ricin A | C | I | Q | M | I | S | E | A | A | R | F | Q | Y | I |
| S06 | A | I | Q | M | T | A | E | A | A | R | F | R | Y | I |
| Trichosanthin | L | I | Q | S | T | S | E | A | A | R | Y | K | F | I |
| Luffin-a | I | L | Q | T | T | A | E | A | S | R | F | K | Y | I |

GENOME CODING PHYTOLACCA ANTIVIRAL PROTEIN AND A RECOMBINANT EXPRESSION VECTOR THEREFOR

This is a continuation of application Ser. No. 08/210,396, filed Mar. 17, 1994, now abandoned which is a division of application Ser. No. 08/138,636, filed Oct. 15, 1993 now U.S. Pat. No. 5,348,865.

FIELD OF THE INVENTION

The present invention relates to a novel nucleotide sequence and a recombinant vector, more specifically, a novel genome coding *Phytolacca insularis* antiviral protein ("PIP") isolated from *Phytolacca insularis* Nakai and a recombinant expression vector therefor.

BACKGROUND OF THE INVENTION

Studies on the antiviral proteins from many different plant species, have been carried out, starting from the discovery of pokeweed antiviral protein ("PAP") isolated from crude extract of *Phytolacca americana* L.[see: Irvin, J. D., Arch. Biochem. Biophys., 169:522–528(1975)]. In addition to the PAP, antiviral proteins have been isolated from several plants, e.g., Rich(from *Ricinus communis*)[see: Halling, K. C. et al., Nucleic Acid Res., 13:8019–8033(1985)], Mirabilis antiviral protein("MA P", from *Mirabilis jalapa* L.)[see: Kataoka, J. et al., J. Biol. Chem., 266:8426–8430(1991)] and α-trichosanthin(from *Trichosanthes kirilowii*)[see: Zhang, X. et al., Nature, 321:477–478(1986)]. Said antiviral proteins have been reported to be ribosome inactivating proteins ("RIPs") having RNA N-glycosidase activities[see: Endo, Y. et al., J. Biol. Chem., 263:8735–8739(1988)].

In general, PAP from *Phytolacca americana* L. is classified as PAP-I, PAP-II and PAP-S that appear in spring leaves, summer leaves and seeds, respectively; and it is known that antiserum reactions among these PAPs are different[see: Irvin, J. D. et al., Arch. Biochem. Biophys., 200:418–425 (1980)]. Further, it has been known that ribosome of *Phytolacca americana* L. is depurinated by RNA N-glycosidase activity of PAP. On the other hand, immunoconjugate of PAP with CD4 or CD19 has been reported to inhibit the replication of human immunodificiency virus type 1[see: Jansen, B. et al., Cancer Res., 52:406–412(1992); Kim Y. W. et al., J. Immunol., 144:1257–1262(1990); Myers, D. E. et al., J. Immunol. Methods, 136:221–238(1991)]; in this connection, said PAPs have been supposed to be applicable to the treatment of AIDS. Accordingly, studies on the PAPs in a view of molecular biology have been actively carried out, including the nucleotide sequence analysis of cDNA and structural gene of PAP; precise celluar mechanism of PAP's biological activity; preparation of transgenic plant; and, application of the immunoconjugate.

Under the circumstances, the inventors have made an effort to isolate antiviral protein from *Phytolacca insularis* Nakai originated in Ulung-Do in Korea, which is closely related to *Phytolacca americana* L. in terms of phylogeny.

SUMMARY OF THE INVENTION

In accordance with the present invention, a novel antiviral protein (PIP) from *Phytolacca insularis* Nakai has been discovered; and, the inventors also discovered the nucleotide sequence of genome coding PIP is novel.

Further, the inventors developed a recombinant vector for said PIP genome expression and a microorganism transformed therewith.

A primary object of the present invention is, therefore, to provide a novel nucleotide sequence of PIP genome.

Another objects of the present invention are to provide a novel recombinant vector for PIP expression and a microorganism transformed therewith.

BRIEF DESCRIPTION OF DRAWINGS

The above and the other objects and features of the present invention will become apparent from following descriptions given in conjunction with the accompanying drawings, in which:

FIGS. 2A and 2B illustrate a full nucleotide sequence of PIP genome isolated from cDNA of *Phytolacca insularis* Nakai and amino acid sequence translated therefrom;

FIG. 3 is a comparative diagram illustrating the amino acid sequence homology of the active sites of PIP and the other ribosome inactivating proteins(RIPs);

DETAILED DESCRIPTION OF THE INVENTION

Figure 1:
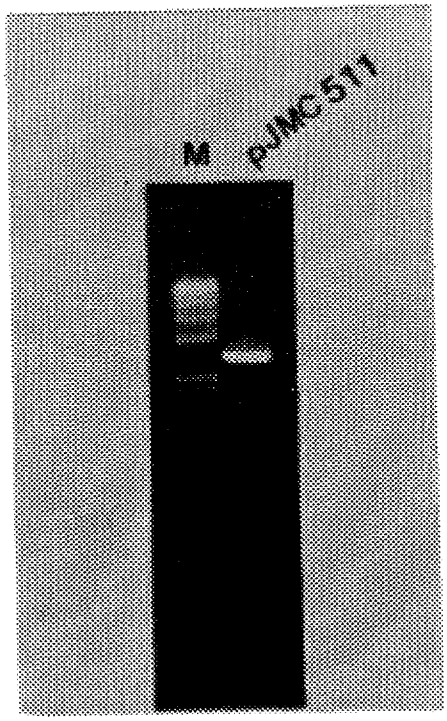
FIG. 1 is a photograph showing agarose gel electrophoresis pattern of pJMC511 containing PIP genome.

To isolate a genome coding PIP, mRNA is purified from leaves of *Phytolacca insularis* Nakai and cDNA library construction thereof is followed; and, PIP genome is isolated by employing PAP genome. Deletion mutant is prepared using Erase-a-Base system(Promega, U.S.A.); and full DNA nucleotide sequence of PIP is determined by Sanger's dideoxy chain termination method[see: Sanger, F., Science, 214:1205–1210(1981)].

For the expression of isolated PIP gene, commercially available FLAG™ vector(International Biotechnologies Inc., U.S.A.) is employed. Since isolated PIP genome has signal peptide, coding region is synthesized using N-terminal primer and C-terminal primer. Amplified DNA is electroeluted, digested with HindIII, ligated into FLAG™ and expression vector pMS12 is prepared. Said pMS12 is deposited with the Korean Collection of Culture and Microorganism(KCCM), an international depository authority(IDA) on Aug. 28, 1993 as deposition No. KCCM 10040.

pMS12 thus prepared is transformed into competent *E. coli* HB101 strain treated with $CaCl_2$ and colonies harboring pMS12 are selected. PIP is induced by culturing said strain on LB broth media containing IPTG(isopropyl-β-D-thiogalactoside) and ampicillin for 6 hrs. After PIP induction, cells thus cultured are harvested, washed with phosphate buffered saline(PBS: 0.01M $NaH_2PO_4$, 0.15M NACl, pH 7.4) solution two times; and lysis of cell pellet is carried out by freezing in dry ice-methanol bath and thawing at 37° C. Centrifugation is followed and supernatant thereof are collected. For the purification of recombinant PIP, said supernatant is loaded on anti-FLAG M1 affinity column and eluted with the PBS solution containing 1.0 mM $CaCl_2$. Synthesis of PIP is determined by SDS-PAGE after synthesis of protein employing in vitro translation technology.

The present invention is further illustrated in the following examples, which should not be taken to limit the scope of the invention.

EXAMPLE 1

Isolation and nucleotide sequence determination of PIP genome 10 g of the leaves of *Phytolacca insularis* Nakai was homogenated using liquid nitrogen. To the homogenate thus prepared was added buffer solution(0.18M Tris, 0.09M LiCl, 4.5 mM EDTA, 1% SDS) for RNA isolation; and centrifugation at 10,000 rpm for 20 min was followed. To eliminate protein and impurities from supernatant, phenol/chloroform extraction and chloroform extraction were carried out in a serial manner; and total RNA was isolated from the supernatant after LiCl sedimentation. mRNA was isolated from total RNA using oligo(dT) cellulose column chromatography, and 5 μg of mRNA thus isolated was used for cDNA synthesis employing ZAP-cDNA synthesis kit (Stratagene, U.K.). Synthesized cDNA was linked to EcoRI adapter, and fractionated by Sephacryl S-400 spun column in accordance with molecular size of cDNA. cDNA thus fractionated was ligated to Uni-Zap XR vector(Stratagene, U.K.), and in vitro packaging employing packaging extract was followed.

To isolate PIP genome from the cDNA library prepared, PAP genome was isolated from cDNA library of *Phytolacca americana* L. and, 0.5 kb EcoRI fragment of said PAP genome was labelled with DIG-Labeling & Detection kit (Boehringer Mannheim, Germany); and, product thus obtained was employed as a probe for PIP gene isolation. *E. coli* XL1-Blue was infected with phage on petri dish to form plaque of $2\times10^4$ pfu and incubated at 37° C. for 12 hrs. 5 clones were obtained from the 1st screening procedure and 2nd screening was followed in a similar fashion as above, with the exception of changing plaque number of $5\times10^2$ pfu. To transfer phagemids of 4 recombinant Uni-Zap XR phages obtained from the 2nd screening, in vivo excision technique employing R408 helper phage was carried out. Plasmids were isolated by alkali lysis method from the B colonies thus selected, and colonies harboring PIP genome were screened by double restriction with EcoRI and XhoI.

To determine nucleotide sequence of PIP genome, the clone 5 was selected from the isolated colonies, and subcloned on pBlueScript SK(-) vector. The clone 5 DNA was double restricted with EcoRI and XhoI, subjected to self ligation, and transformed into competent XL1-Blue. The clones cultured on LB media(10 g/l Bactotrypton, 5 g/l Yeast extract, 5 g/l NaCl, pH 7.5) containing 50 μg ampicillin, were selected and plasmids were isolated by alkali lysis method, and colonies harboring 0.7 kb and 0.5 kb EcoRI/XhoI fragment were selected.

FIG. 1 shows an electrophoresis pattern of pJMC511 harboring PIP genome(M is λDNA digested with HindIII which is employed as molecular size marker). DNA obtained from each colonies was isolated and nucleotide sequence of PIP cDNA insert was determined by dideoxy chain termination method employing Sequenase(United States Biochemical, U.S.A.) and primers such as SK promoter primer and T7 promoter primer. Plasmid thus sequenced was named pJMC511, and deposited with the Korean Culture Center of Microorganisims(KCCM) on Aug. 28, 1993 as deposition No. KCCM 10041.

Meanwhile, as disclosed in FIG. 2, PIP cDNA is consist of 918 bp of one open reading frame and termination codon; and polyadenylation signal which is ubiquitous in mRNA of most plants and animals, appears to be located in the upstream of 33 bp from the polyadenylation site. In FIG. 2, (*) is termination code, and amino acid sequence was written out in accordance with IUPAC nomenclature system.

From the study on nucleotide sequence homology of said PIP genome and PAP genome isolated from cDNA library of *Phytolacca americana* L., nucleotide sequence homology of about 82% was determined; and, it was also confirmed that PIP cDNA insert codes 305 amino acid residues and 22 residues of which function as signal peptide analogously in the case of PAP. Compared with amino acid sequence of PAP genome, high level of homology of about 81% was determined; and amino acid sequence for active site of PIP and PAP was appeared to be completely same.

As disclosed in FIG. 3, amino acid sequences prevalent in ribosome-inactivating proteins(RIPs: PAP, Abrin A chain, Luffin-a, MAP, Ricin A chain, Trichosanthin and S06) are also found in PIP genome(Ile-Gln-Met-Val-Ser-Glu-Ala-Arg-Phe-Lys-Tyr-Ile), which is assumed to be the active site of RIPs.

EXAMPLE 2

Preparation of expression vector pMS12

Figure 5:
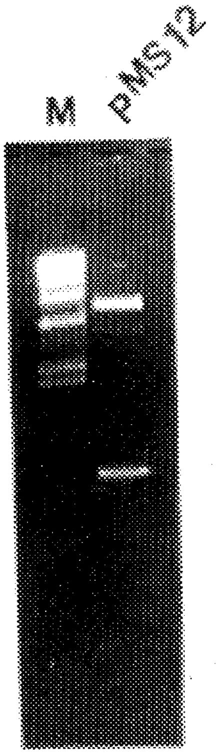
FIG. 5 is a photograph showing agarose gel electrophoresis pattern of expression vector pMS12.
Figure 4:
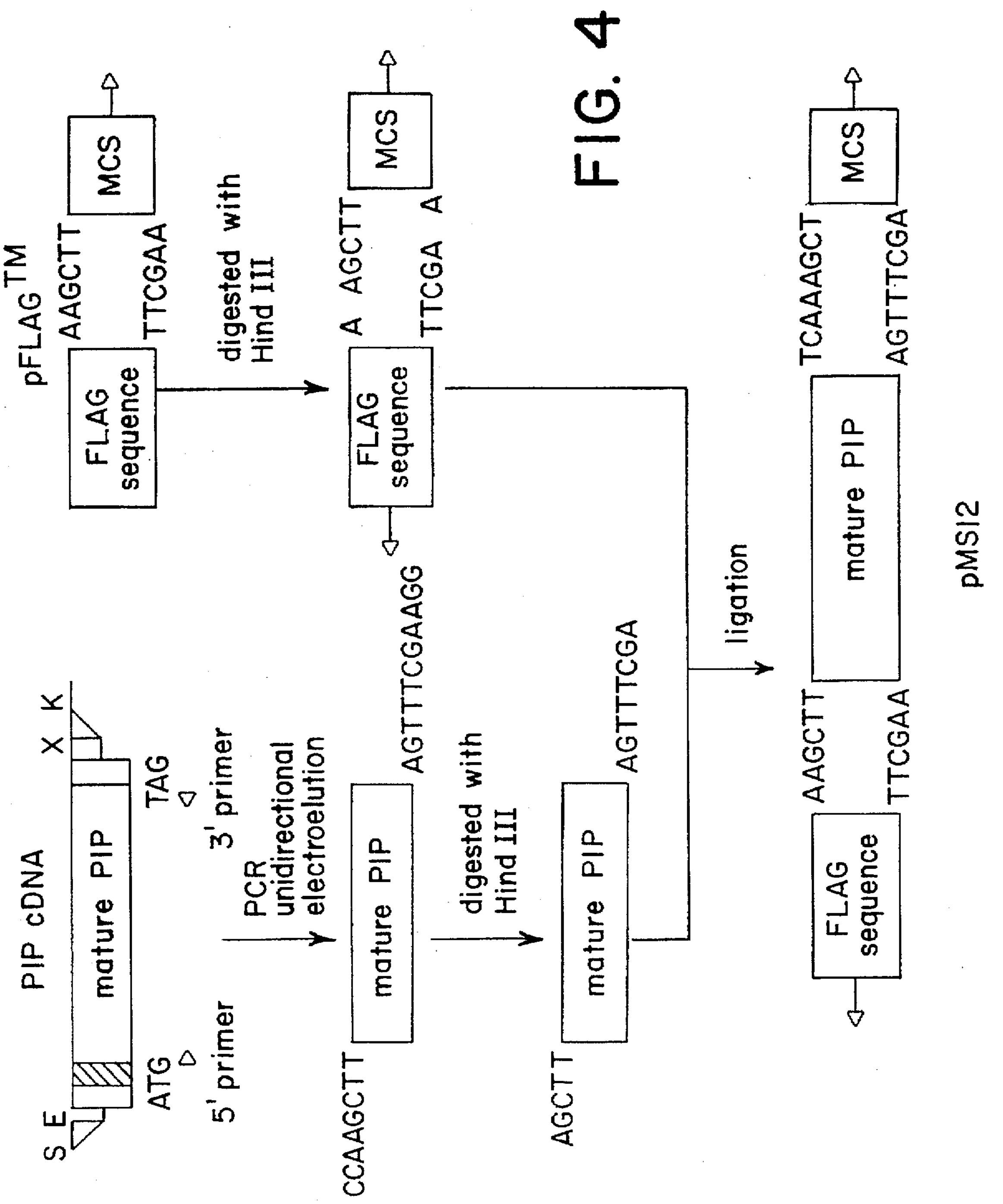
FIG. 4 is a scheme depicting stepwise construction strategy for expression vector pMS12 of the invention.

For the expression of PIP genome in *E. coli* HB101, commercially available FLAG™ vector(International Biotechnologies Inc., U.S.A.) was employed. Primers such as 5'-CCAAGCTTGTGAATACCATCATCTA C-3' and 5'-GGAAGCTTAAACTAATCACCAAGATT-3' synthesized by DNA Synthesizer(Applied Biosystems Inc., U.S.A.), were employed as N-terminal primer and C-terminal primer, respectively; and PIP genome was amplified by polymerase chain reaction using Vent™ DNA polymerase(New England Biolab., U.S.A.). In this connection, denaturation(95° C., 30 sec), annealing(55° C., 30 sec) and extension(72° C., 30 sec) were carried out for 30 cycles by DNA Thermal Cycler (Cetus/Perkin-Elmer, U.S.A.). PIP genome thus amplified was cleaved with HindIII, and expression vector of the invention was prepared by ligating HindIII-cleaved PIP gene into HindIII-cleaved FLAG™ vector with $T_4$ DNA ligase. Expression vector thus prepared was named pMS12; and deposited with the Korean Culture Center of Microorganisims(KCCM) on Aug. 28, 1993 as deposition No. KCCM 10040. The process for stepwise constructing pMS12 is illustrated in FIG. 4. In FIG. 4, 'MCS' is employed to mean multicloning site.

pMS12 thus constructed was transformed into competent *E. coli* HB101 prepared by the treatment of $CaCl_2$ solution; and, transformant harboring pMS12 was selected from the colonies cultured on LB media containing 50 μg/ml ampicilin, based on plasmid DNA isolation technique employing alkaline lysis method[see: Maniatis et al., Molecular Cloning, 368–369(1982)]. FIG. 5 is a photograph showing 0.8% agarose gel electrophoresis pattern of pMS12 digested with HindIII. In FIG. 5, M is molecular size marker, i.e., λDNA cleaved with HindIII, and pMS12 lane shows expression vector pMS12 of the present invention.

EXAMPLE 3

Growth inhibition of microorganism transformed with pMS12

Figure 6:
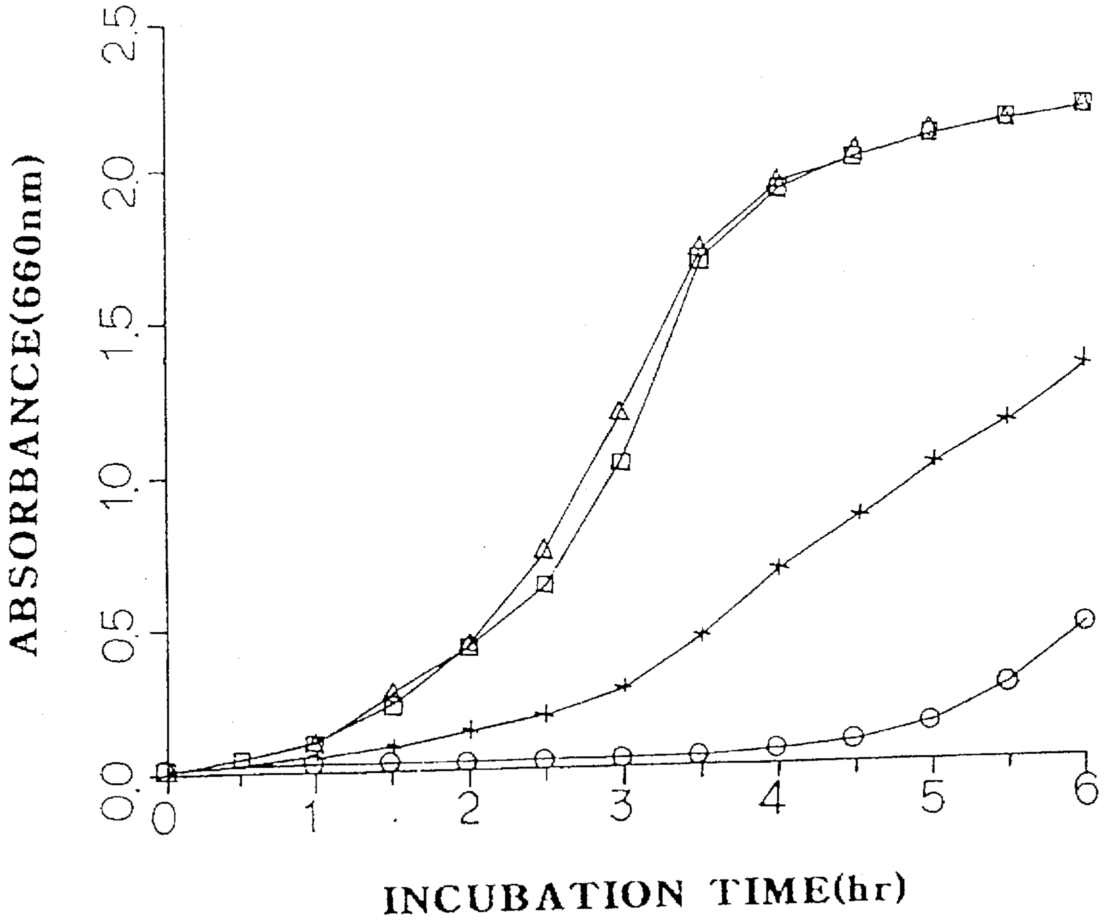
FIG. 6 is a graph showing growth pattern of HB101 harboring pMS12.

Expression of PAP and MAP genome has been reported to inhibit growth of host microorganism transformed therewith. On the other hand, genome of Ricin which is a kind of RIP, has been reported not to inhibit growth of its transformant. Under the circumstance, whether recombinant PIP inhibits growth of transformant or not, was studied through the investigation of cell growth pattern. Non-transformed *E. coli* HB101 and transformed *E. coli* HB101 harboring pFLAG or pMS12 were inoculated on LB media containing 50 μg/ml ampicilin, and incubated overnight. Cultures of the same cell concentration thus incubated were inoculated on LB liquid media containing 0.7 mM IPTG(isopropyl-β-D-thiogalactoside), cultured on shaking incubator at 37° C.; and, cell concentrations were measured as absorbance at 600 nm. As clearly disclosed in FIG. 6, the growth of HB101 harboring pMJ12(o-o) which produce recombinant PAP (KCCM 10037) and HB101(*-*) harboring pMS12 which produce recombinant PIP was inhibited remarkably, while that of non-transformed HB101(Δ-Δ) and transformed HB101(□-□) harboring pFLAG was normal. Accordingly, it was dearly determined that recombinant PIP inhibits the growth of *E. coli* HB101 transformed with pMS12, analogously in the case of PAP.

EXAMPLE 4

Isolation of recombinant PIP from *E. coli* HB101 transformed with vector pMS12

*E. coli* HB101 harboring pMS12 was cultured on 50 ml of LB medium containing 50 μg/ml ampicilin; and recombinant PIP was induced by the addition of 0.75 mM of IPTG when $OD_{600}$ was reached to 1.0. After PIP induction, cells thus cultured were harvested by centrifugation, washed 2 times with phosphate buffered saline(PBS: 0.01M $NaH_2PO_4$. 0.15M NaCl, pH 7.4); and, subjected to freezing in dry ice-methanol bath and thawing at 37° C. Then, cell thus treated was emulsified with said buffer solution(pH 8.4) containing 0.25 mg/ml lysozyme; and freezing in dry ice-methanol bath and thawing process was repeated 3 times. Said solution was shaked at an interval of 10 min, kept in 37° C. for 30 min and centrifuged at 25,000×g for 45 min at 4° C. 10 μl of supernatant thus obtained was analyzed by 10% SDS-PAGE, stained with Coomassie brilliant blue R, and destained with destaining solution; and production of recombinant PIP was determined.

Figure 7:
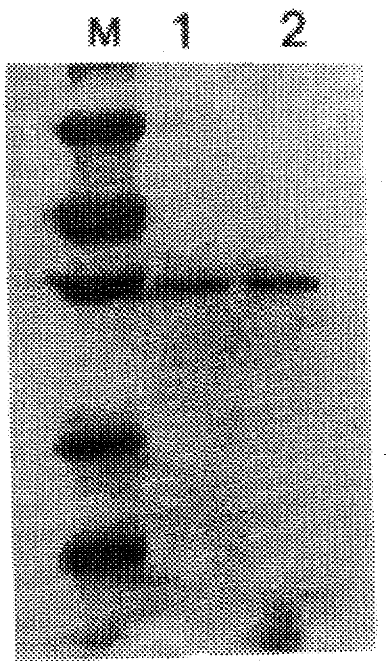
FIG. 7 is a photograph showing SDS-PAGE pattern of proteins purified from *E. coli* HB101 harboring pMS12; and, FIG. 8 is a photograph showing SDS-PAGE pattern of in vitro translation of purified PIP.

To the said supernatant was added 1M $CaCl_2$ solution, to the final concentration of 1.0 mM and said solution was loaded on anti-FLAG M1 affinity gel column, after washing with 5 ml of glycine-HCl(pH 3.0) and PBS solution 3 times, and with 12 ml PBS/Ca solution(PBS solution containing 1.0 mM $CaCl_2$) 3 times. 500 μl of PBS/EDTA solution(PBS solution containing 2.0 mM EDTA) was kept for 30 min in the column to which recombinant PIP was bound; and eluted with 500 μl PBS/EDTA solution(PBS solution containing 2.0 mM EDTA) at an interval of 10 min. Amount and purity of recombinent PIP thus isolated were determined by absorbance measurement and SDS-PAGE analysis, respectively. FIG. 7 is a photograph showing SDS-PAGE pattern of purified recombinant PIP(lane 2) and recombinant PAP(lane 3).

EXAMPLE 5

Activity determination of recombinant PIP

For the activity determination of the purified recombinant PIP which inhibits protein synthesis, in vitro translation employing rabbit reticulocyte lysis system(Promega, U.S.A.) was carried out. Recombinant PIP purified in accordance with the Example 4 and dialysed against deionized water by Spectra/Por 2 membrane(Spectrum, U.S.A.) system, was employed to compare with the activity of recombinant PAP.

The reaction mixtures for in vitro translation were disclosed in Table 1.

TABLE 1

Reaction mixtures for in vitro translation

| experimental group | control | PIP | PAP |
|---|---|---|---|
| reaction mixture | 35 μl rabbit reticulocyte lysate<br>1 μl $^{35}$S-methionine (10 mCi/ml)<br>1 μl RNasin (40 U/μl)<br>2 μl luciferase RNA (0.5 μg/μl)<br>11 μl Water | 35 μl rabbit reticulocyte lysate<br>1 μl $^{35}$S-methionine (10 mCi/ml)<br>1 μl RNasin (40 U/μl)<br>2 μl luciferase RNA (0.5 μg/μl)<br>11 μl recombinant PIP (80 pmol) | 35 μl rabbit reticulocyte lysate<br>1 μl $^{35}$S-methionine (10 mCi/ml)<br>1 μl RNasin (40 U/μl)<br>2 μl luciferase RNA (0.5 μg/μl)<br>11 μl recombinant PAP (80 pmol) |

Figure 8:
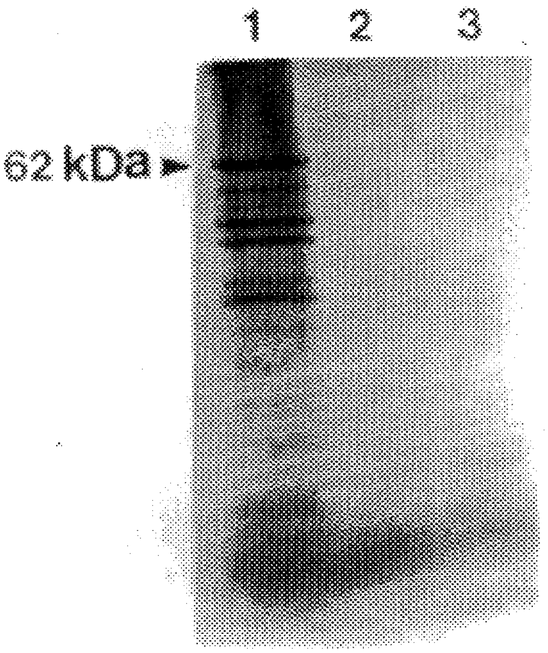

Each experimental group was incubated at 37° C. for 90 min. Proteins thus synthesized were fractionated by 15% SDS-PAGE, dried with gel dryer and determined by radioautography. FIG. 8 is a photograph showing the results of SDS-PAGE after in vitro translation experiment. As clearly illustrated in FIG. 8, protein synthesis of luciferase(62 KD) is appeared in control group(lane 1), while recombinant PIP(lane 3) and recombinent PAP(lane 2) do not show any protein synthesis.

As clearly illustrated and demonstrated as aboves, the present invention provides a novel genome of PIP isolated from *Phytolacca insularis* Nakai, which is a kind of ribosome inactivating proteins, and a recombinant expression vector producing said PIP.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 918 base pairs
( B ) TYPE: nucleic acid
( C ) STRANDEDNESS: single -continued ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( A ) ORGANISM: Phytolacca insularis ( v i i ) IMMEDIATE SOURCE:
( B ) CLONE: antiviral protein (PIP)

( x i ) SEQUENCE DESCRIPTION: SEQ ID NO:1:

```
ATGAAGTTGA TGCTTGTGGT GACAATATCA GTATGGCTCA TTCTTGCACC AACATCTACT    60
TGGGCCGTGA ATACCATCAT CTACCATGTT GGAAGTACCA CCATTAGAAA CTATGCAACT   120
TTTGGATACT TCGTACTGAA GGCGAAGATC CAAGTTATGT GCTATGGAAT ACCAATGCTG   180
CCCAATATTG GATCAAATCC AAAATACATA TTGGTTGAGC TCCAAGGTTC AAATGAAGAA   240
GGCATCACAC TAATGCTAAG ACGAAACAAT TTATATGTGA TGGGCTATTC TGATCCCTAC   300
AACAATAGGT GTCGTTTCCA TCTCTTTAAG GCTATCTCAG GTACTGAACG CGAAGATGTA   360
GAGACTACTC TTTGCCCAAA TGCCGATTCT CGTGTTGGTA AAAACATAAA CTATGATAGT   420
CGATATCCAA CATTGGAATC AAAAGCAGGA GTAAATTCAA GAAGTCGAGT CCAACTGGGA   480
ATTCGAATAC TCGACAGTGG CATTGGAAGG ATTTCTGGAG TGACGTCATT CACTGAGAGA   540
ACCGAAGCTG AATTCCTACT GGTAGCCATA CAAATGGTAT CAGAGGCAGC AAGATTCAAG   600
TACATAGAGG ATCAAGTGAA AACTAATTTT AACAGACCAT TCAACCCTAA TCCCAAAGTA   660
CTTATATTGC AGGAGACATG GGGTAAGATT TCTTCAGCAA TTCATGGTGC CAGGAATGGA   720
GTTTTACCCA ATCCTCTACA GCTAGTGCAT GCCAATGGTG CAAATTGGAT AGTGTTGAGA   780
GTGGATGAAA TCAAGCCTGA TGTGTCACTC TTAAACTACG TTATTGGGAG CTGCCAGAGA   840
ACTTATAACC AAAATGCCAT GTTTTCTCAA CTTATAATGT CTACTTATTA TAATTACATG   900
GCTAATCTTG GTGATTAG                                                 918
```

( 2 ) INFORMATION FOR SEQ ID NO:2:

( i ) SEQUENCE CHARACTERISTICS:
( A ) LENGTH: 305 amino acids
( B ) TYPE: amino acid
( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
( A ) ORGANISM: Phytolacca insularis ( v i i ) IMMEDIATE SOURCE:
( B ) CLONE: antiviral protein (PIP)

( x i ) SEQUENCE DESCRIPTION: SEQ ID NO:2:

```
Met Lys Leu Met Leu Val Val Thr Ile Ser Val Trp Leu Ile Leu Ala
1               5                   10                  15

Pro Thr Ser Thr Trp Ala Val Asn Thr Ile Ile Tyr His Val Gly Ser
            20                  25                  30

Thr Thr Ile Arg Asn Tyr Ala Thr Phe Gly Tyr Phe Val Leu Lys Ala
        35                  40                  45

Lys Ile Gln Val Met Cys Tyr Gly Ile Pro Met Leu Pro Asn Ile Gly
```

-continued 50 55 60

Ser Asn Pro Lys Tyr Ile Leu Val Glu Leu Gln Gly Ser Asn Glu Glu
65 70 75 80

Gly Ile Thr Leu Met Leu Arg Arg Asn Asn Leu Tyr Val Met Gly Tyr
85 90 95

Ser Asp Pro Tyr Asn Asn Arg Cys Arg Phe His Leu Phe Lys Ala Ile
100 105 110

Ser Gly Thr Glu Arg Glu Asp Val Glu Thr Thr Leu Cys Pro Asn Ala
115 120 125

Asp Ser Arg Val Gly Lys Asn Ile Asn Tyr Asp Ser Arg Tyr Pro Thr
130 135 140

Leu Glu Ser Lys Ala Gly Val Asn Ser Arg Ser Arg Val Gln Leu Gly
145 150 155 160

Ile Arg Ile Leu Asp Ser Gly Ile Gly Arg Ile Ser Gly Val Thr Ser
165 170 175

Phe Thr Glu Arg Thr Glu Ala Glu Phe Leu Leu Val Ala Ile Gln Met
180 185 190

Val Ser Glu Ala Ala Arg Phe Lys Tyr Ile Glu Asp Gln Val Lys Thr
195 200 205

Asn Phe Asn Arg Pro Phe Asn Pro Asn Pro Lys Val Leu Ile Leu Gln
210 215 220

Glu Thr Trp Gly Lys Ile Ser Ser Ala Ile His Gly Ala Arg Asn Gly
225 230 235 240

Val Leu Pro Asn Pro Leu Gln Leu Val His Ala Asn Gly Ala Asn Trp
245 250 255

Ile Val Leu Arg Val Asp Glu Ile Lys Pro Asp Val Ser Leu Leu Asn
260 265 270

Tyr Val Ile Gly Ser Cys Gln Arg Thr Tyr Asn Gln Asn Ala Met Phe
275 280 285

Ser Gln Leu Ile Met Ser Thr Tyr Tyr Asn Tyr Met Ala Asn Leu Gly
290 295 300

Asp
305

What is claimed is:

1. Phytolacca antiviral protein isolated from *Phytolacca insularis* Nakai comprising the amino acid sequence:

Met Lys Leu Met Leu Val Val Thr Ile Ser
1 5 10

Val Trp Leu Ile Leu Ala
15

Pro Thr Ser Thr Trp Ala Val Asn Thr Ile
20 25

Ile Tyr His Val Gly Ser
30

Thr Thr Ile Arg Asn Tyr Ala Thr Phe Gly
35 40 45

Tyr Phe Val Leu Lys Ala

Lys Ile Gln Val Met Cys Tyr Gly Ile Pro
50 55 60

Met Leu Pro Asn Ile Gly

-continued

Ser Asn Pro Lys Tyr Ile Leu Val Glu Leu
65 70 75

Gln Gly Ser Asn Glu Glu
80

Gly Ile Thr Leu Met Leu Arg Arg Asn Asn
85 90

Leu Tyr Val Met Gly Tyr
95

Ser Asp Pro Tyr Asn Asn Arg Cys Arg Phe
100 105

His Leu Phe Lys Ala Ile
110

Ser Gly Thr Glu Arg Glu Asp Val Glu Thr
115 120 125

Thr Leu Cys Pro Asn Ala

Asp Ser Arg Val Gly Lys Asn Ile Asn Tyr
130 135 140

-continued

Asp Ser Arg Tyr Pro Tyr

Leu Glu Ser Lys Ala Gly Val Asn Ser Arg
145 150 155

Ser Arg Val Gln Leu Gly
160

Ile Arg Ile Leu Asp Ser Gly Ile Gly Arg
165 170

Ile Ser Gly Val Thr Ser
175

Phe Thr Glu Arg Thr Glu Ala Glu Phe Leu
180 185

Leu Val Ala Ile Gln Met
190

Val Ser Glu Ala Ala Arg Phe Lys Tyr Ile
195 200

Glu Asp Gln Val Lys Thr
205

Asn Phe Asn Arg Pro Phe Asn Pro Asn Pro
210 215 220

Lys Val Leu Ile Leu Gln

Glu Thr Trp Gly Lys Ile Ser Ser Ala Ile
225 230 235

His Gly Ala Arg Asn Gly
240

-continued

Val Leu Pro Asn Pro Leu Gln Leu Val His
245 250

Ala Asn Gly Ala Asn Trp
255

Ile Val Leu Arg Val Asp Glu Ile Lys Pro
260 265

Asp Val Ser Leu Leu Asn
270

Tyr Val Ile Gly Ser Cys Gln Arg Thr Tyr
275 280

Asn Gln Asn Ala Met Phe
285

Ser Gln Leu Ile Met Ser Thr Tyr Tyr Asn
290 295 300

Tyr Met Ala Asn Leu Gly

Asp.
305

2. *Phytolacca insularis* antiviral protein produced by the process comprising the step of culturing *E. coli* HB101 transformed with the expression vector pMS12 (Accession No. KCCM 10040).

* * * * *